United States Patent [19]

Gussin et al.

[11] 3,934,007

[45] Jan. 20, 1976

[54] METHOD OF REMOVING TOXIC SUBSTANCES FROM THE INTESTINAL TRACT BY THE USE OF A SURFACTANT AND A SORBENT

[75] Inventors: Robert Zalmon Gussin, Suffern, N.Y.; Lewis Smith Meriwether, Westport, Conn.

[73] Assignee: American Cyanamid Company, Stamford, Conn.

[22] Filed: Mar. 27, 1974

[21] Appl. No.: 455,455

Related U.S. Application Data

[63] Continuation-in-part of Ser. No. 373,068, June 25, 1973, abandoned.

[52] U.S. Cl. .................. 424/125; 424/79; 424/180; 424/313; 424/319; 424/333
[51] Int. Cl.² ................ A61K 31/225; A61K 33/43
[58] Field of Search .................... 424/125, 313, 180

[56] References Cited
UNITED STATES PATENTS
3,642,986   2/1972   Welch et al. .................... 424/125

OTHER PUBLICATIONS

Chemical Abstracts 77:150323m (1972).

Handbook of Non-Prescription Drugs—Pub. by Am. Pharm. Assoc. pp. 73-74—Mar.—1973.

*Primary Examiner*—Leonard Schenkman
*Attorney, Agent, or Firm*—Denis A. Polyn

[57] ABSTRACT

Method of removing metabolic waste products from a warm-blooded animal by orally administering a composition of a non-toxic surfactant and pharmaceutically acceptable sorbents.

The compositions are useful in treating chronic and acute uremia, hepatic failure due to cirrhosis or other causes, acute renal failure such as from drug poisonings and other conditions requiring removal of toxic substances in which oral drug administration is feasible.

5 Claims, No Drawings

METHOD OF REMOVING TOXIC SUBSTANCES FROM THE INTESTINAL TRACT BY THE USE OF A SURFACTANT AND A SORBENT

DESCRIPTION OF THE INVENTION

This invention, broadly speaking, is a method of removing metabolic wastes and toxic substances from warm-blooded animals by orally administering compositions containing a non-toxic surfactant in association with one or more pharmaceutically acceptable sorbents.

It is a well known fact that the presence of large amounts of toxins or toxic substances in the blood stream, both endogenously or exogenously generated, is a threat to the life of the host. The presence of toxic substances is often due to infections, poisoning, partial or total kidney failure and generally debility of the host. In extremely severe cases, the use of hemodialysis machines is necessary to perform the function of clearing the blood stream of toxin and toxic substances when the kidneys are for some reason unable to perform this function. Any method of removing toxins or toxic substances from the blood stream is desirable and aids the kidneys in this respect, and is an aid to the kidneys even though it may not eliminate the use of hemodialysis equipment.

This invention is useful in the treatment of all degrees of renal failure. Although it may not be capable of totally replacing hemodialysis in every case, it can significantly lengthen the interdialytic period. This would greatly reduce the cost of treatment of the patient, increase the comfort of the patient, reduce the risks involved in dialysis, and markedly increase the capacity of dialysis centers so more patients could be treated. The oral treatment described in this invention could also conceivably serve as the sole method of treatment in milder cases of renal failure, providing relief to patients that were previously untreated, and permit long term survival without dialysis.

We have now found that a mixture of surfactants and sorbents used orally in the treatment of uremia or hepatic failure offers advantages of lower cost, greater ease and less discomfort over the classical hemodialysis treatment. The present invention increases the feasibility for successful oral treatment by increasing the rate of movement of toxins into the intestine by the presence of a surfactant and thus, since the toxin concentration is greater, quicker and greater availability of the toxin to a sorbent is available. This results in an increased quantity and rate of uptake of toxin by the sorbent.

The present invention consists in a combination of a surfactant and a sorbent to be administered orally to a warm-blooded animal with uremia or hepatic disease. Uremia is generally the condition resulting from the inability of the kidneys to remove toxic substances from the blood. Liver disease can result in a dangerous rise in the level of ammonia and other toxins and is frequently accompanied by kidney failure.

While applicants do not wish to be bound by any theory, it is believed that the surfactant enhances the permeability of the intestines to uremic toxins and once the toxins have entered the intestines to trap them there with the sorbent. The toxins will then be excreted in the feces and their levels in the blood and body tissues diminished, and hence, their toxic liability decreased.

It is known to use oxystarch in the removal of urea and ammonia from the gut (Carmello Giordano, et al. "Trapping of Urea and Ammonia in the Gut of Uremic Patients," *Advances in Nephrology*, Vol. 2 1972, Yearbook Medical Publishers). We have found this method can be improved by also having present an exogenous non-toxic surfactant such as dioctylsodium sulfosuccinate or N-lauryl -$\beta$-aminopropionic acid.

The preferred embodiment of our invention is a composition containing an exogenous non-toxic surfactant such as dioctylsodiumsulfosuccinate and a high molecular weight sorbent such as those of the group of activated carbons including Darco S-51 or G-16, Pittsburg SGL, Columbia LC, Norit A Norit USP XVIII, Barnebey Cheney XH-2 or Nuchar C-190-N, Polyaldehydes such as oxystarch, periodate oxidized amylose, periodate oxidized cellulose (oxycellulose), periodate oxidized microcrystalline cellulose, periodate oxidized cotton, periodate oxidized dextran, periodate oxidized dextrin, periodate oxidized polygalacturonic acid, periodate oxidized pectin, periodate oxidized pectinic acid, periodate oxidized agar, periodate oxidized guar gum, periodate oxidized alginic acid, periodate oxidized xylan, periodate oxidized mannosan, periodate oxidized glycogen, periodate oxidized carboxymethyl cellulose. The preparation of periodate oxidized compounds, particularly carbohydrates is described in Advances in Carbohydrate Chemistry, Vol. II, pages 1 to 41 (1956) by J. M. Bobbitt. Other compounds found useful are polyacrolein, polymethacrolein, and copolymers of acrolein and methacrolein with other comonomers, cation exchange resins such as Dowex 50W, Amberlite IRC-50 or CG-50, Chelex 100 or Bio-Rad AG-50W.

The terms oxystarch, dialdehyde starch and oxidized starch are often used interchangeably for the product of periodate oxidation of starch. Similar terminology is used for other polysaccharides.

The surfactants (other than those mentioned above) useful for increasing the serosal to mucosal movement of substances across the gut may be, for example, stearyl dimethylamine, sodium lauryl sulfate, sodium stearate, stearyl trimethylammonium chloride, cetyl trimethylammonium chloride, lauryl trimethylammonium chloride, cetyl pyridinium chloride, tetraheptylammonium chloride, polysorbate 80, stearyl dimethylamine, dimethylaminoethanol, tris(hydroxymethyl)aminomethane, dodecylammonium chloride, hexadecylamine, octadecylamine, heptylamine, triethanolamine, ethylenediamine, hexadecylmorpholine, ethylenediamine tetraacetic acid, para-aminobenzoic acid, anthranilic acid and N-myristyl-$\beta$-aminopropionic acid and the like.

The amount of sorbent for each unit of non-toxic surfactant may vary from about 10 to 10,000 times the surfactant.

There may also be present in addition to the active components a pharmaceutically acceptable carrier. This carrier can be those ingredients well known to those skilled in the art in the preparation of tablets, powders, dispersible granules, capsules, microcapsules and cachets. The carrier may be one or more substances which may also act as flavoring agents, binders, tablet disintegrating agents or an encapsulating material. In the preparation of tablets the active components are mixed with a carrier having the necessary binding properties in suitable proportions and compacted in the size and shape desired. Suitable solid carriers are, for example, magnesium carbonate or stearate, talc, sugar, lactose, pectin, dextrin, starch, gelatin, tragacanth, methyl cellulose, ethyl cellulose, or sodium carboxymethyl cellulose, cellulose acetate phthalate or polyvinyl acetate phthalate.

SPECIFIC EXAMPLES

The following examples describe experiments carried out to show the superiority of compositions containing a surfactant and a pharmaceutically acceptable sorbent and compositions useful in the present invention. Examples 1, 2 and 5 illustrate the enhanced movement of uremic toxins from serosal to mucosal side of the intestine resulting from presence of surfactant. Examples 3 and 4 demonstrate the increased uptake of uremic toxins by sorbents in the gut in the presence of surfactant. The other examples show other aspects of the invention.

EXAMPLE 1

An experiment is carried out similar to the process described in Example 3 hereinafter, except that the bath is made up of buffer solution containing urea (100 mg.%) and dioctylsodium sulfosuccinate.

TABLE I

Milligrams of urea removed from bath containing urea or urea-dioctyl sodium sulfosuccinate

| Time (minutes) | Urea and No DSS* | Urea-DSS both sides | Urea-DSS inside only |
| --- | --- | --- | --- |
| 15 | 0.206 | — | — |
| 30 | 0.386 | 0.503 | 0.506 |
| 60 | 0.536 | 0.750 | 0.743 |
| 120 | 0.813 | 1.036 | 0.263 |
| 240 | 0.980 | 1.096 | 1.256 |

*DSS is dioctyl sodium sulfosuccinate.

The urea alone shows the lowest removal of urea from bath.

EXAMPLE 2

An experiment is carried out similar to the process described in Example 3 except that the bath is made up of creatinine (4 mg.%) and 0.001% or 0.01% dioctyl sodium sulfosuccinate.

TABLE II

Milligrams of Creatinine Removed from Bath

| Time | No DSS | .001% DSS, only | .01% DSS, sac only | .01% DSS, Both Sides | 0.01% (pre soak in sac buffer) |
| --- | --- | --- | --- | --- | --- |
| 15 | 0.17 | 0.17 | — | — | 0.44 |
| 30 | 0.28 | 0.34 | 0.43 | 0.65 | 0.62 |
| 60 | 0.41 | 0.63 | 0.73 | 0.72 | 0.93 |
| 120 | 0.64 | 0.86 | 1.12 | 1.09 | 1.16 |
| 240 | 0.81 | 0.99 | 1.17 | 1.19 | 1.19 |

The above experiment shows that when dioctyl sodium sulfosuccinate is not present, the lowest results are obtained and also demonstrates the dose dependent nature of the effect of DSS.

EXAMPLE 3

Rats were killed by a sharp blow on the head and the abdomen was immediately opened and the entire small intestine removed. The intestine was flushed with buffer (Krebs-Henseleit buffer) and cut into segments of approximately 3 cm. in length. These were filled by use of a syringe and blunt needle after tying one end. Simultaneous withdrawal of the needle from the end of the segment and tightening of a ligature at that end resulted in the formation of sausage-like sacs of intestine with 1 ml. of desired medium inside. The medium in different segments consisted of (1) plain buffer solution, (2) buffer solution with added activated carbon (30 g./L) and (3) buffer solution with activated carbon (30 g./L) and dioctyl-sodium sulfosuccinate (0.01%). The sacs were placed in an Erlenmeyer flask containing 2 ml. of 4 mg. percent creatinine. The flasks were placed in a Dubnoff incubating shaker under an atmosphere of 95% oxygen and 5% carbon dioxide.

The temperature of the bath was maintained at 37°C. and flasks shaken throughout the experiment. At the end of appropriate incubation periods, the flasks were removed and the contents of the bath and sacs analysed. The following results were obtained.

TABLE III

Creatinine (mg.%) remaining in bath which at start of experiment contains 4 mg. percent

| Time (minutes) | Sac + buffer | Sac + Activated Carbon | Sac + Activated Carbon + Dioctyl sodium sulfosuccinate |
| --- | --- | --- | --- |
| 15 | — | — | 3.13 |
| 30 | — | 3.4 | 2.83 |
| 60 | 3.28 | 2.8 | 2.43 |
| 120 | 3.0 | 2.63 | 1.63 |
| 240 | 2.83 | 1.83 | 1.07 |

The above results show that the sorbent and surfactant when used together produce the greatest amount of creatinine removal from the bath.

EXAMPLE 4

Following the procedure described in Example 3 and substituting 20 mg. of ammonium hydrogen carbonate (0.1 M.) in place of creatinine in the bath, along with 250 mg. oxystarch in place of charcoal in the sac, the following results were obtained on analysis.

TABLE IV

Millimoles of Ammonia Removed From Bath Containing Ammonium Hydrogen Carbonate (0.1 M.)

| Time (minutes) | Sac + buffer | Sac + oxystarch | Sac + oxystarch + dioctylsodium sulfosuccinate (.01%) |
| --- | --- | --- | --- |
| 15 | 0 | 0.041 | 0.073 |
| 30 | 0.058 | 0.088 | 0.146 |
| 60 | 0.098 | 0.139 | 0.18 |
| 120 | 0.104 | 0.248 | 0.346 |
| 240 | 0.138 | 0.374 | 0.473 |

The above results show that the oxystarch (Sumstar 190, Miles Laboratories) and dioctyl sodium sulfosuccinate when used together produce the greatest removal of ammonia from the bath.

EXAMPLE 5

Following the procedure described in Example 3 but omitting the activated carbon and using 0.01% N-lauryl-$\beta$-amino-propionic acid or dioctyl sodium sulfosuccinate, the following results are obtained.

TABLE V

Creatinine (mg.%) Remaining in Bath at the Time Interval Shown

| Time (minutes) | Sac + Buffer | Sac + DSS | Sac + N-lauryl-β-aminopropionic acid |
|---|---|---|---|
| 0 | 4.0 | 4.0 | 4.0 |
| 30 | 3.4 | 3.0 | 3.1 |
| 60 | 3.3 | 2.9 | 2.7 |
| 120 | 3.0 | 2.6 | 2.6 |
| 240 | 2.9 | 2.4 | 2.5 |

The above experiment shows that when a surfactant is not present, the greatest amount of creatinine remains in the bath.

EXAMPLE 6

Following the procedure described in Example 3 but using both oxystarch and activated carbon together inside the sac (at the same levels used in Examples 3 and 4 respectively) along with 0.01% dioctyl sodium sulfosuccinate, and both 4 mg. percent creatinine and 0.1M ammonium hydrogen carbonate in the bath, essentially the same results for removal of toxins from the bath are obtained using the sorbents in combination as in Examples 3 and 4 when the sorbents are used separately.

EXAMPLE 7

Using the procedure described in Example 4 but substituting 250 mg. of Amberlite CG-50 (200–400 mesh) cation exchange resin for the oxystarch inside the sac, results similar to those of Example 4 are obtained in which the amount of ammonia removed from the bath is greatest in the presence of both sorbent and surfactant.

EXAMPLE 8

Following the procedure described in Example 6 but substituting Amberlite CG-50 resin for the oxystarch, essentially the same results for removal of toxins from the bath are obtained using the sorbents in combination as in Examples 3 and 7 wherein the sorbents are used separately.

EXAMPLE 9

|  | Grams |
|---|---|
| Dioctylsodiumsulfosuccinate | 1.00 |
| Oxystarch | 25.00 |
| Sucrose | 25.00 |
| Starch | 22.00 |
| Acacia | 7.8 |
| Talc | 3.1 |
| Magnesium stearate | 1.5 |
| Stearic acid | 1.6 |

Mix thoroughly and compress into 100 tablets.

EXAMPLE 10

|  | Grams |
|---|---|
| Dioctylsodiumsulfosuccinate | 1.50 |
| Activated Carbon | 50.00 |
| Corn starch | 150.00 |
| Magnesium stearate | 25.00 |
| Hard gelatin capsules 1000 |  |

The finely powdered ingredients are mixed thoroughly until uniformly dispersed and then filled into hard gelatin capsules of appropriate size.

EXAMPLE 11

|  | Grams |
|---|---|
| Dioctylsodiumsulfosuccinate | 1.00 |
| Amberlite resin | 25.00 |
| Sucrose | 25.00 |
| Starch | 22.00 |
| Acacia | 7.8 |
| Talc | 3.1 |
| Magnesium stearate | 1.5 |

Mix thoroughly and compress into 100 tablets.

EXAMPLE 12

|  | Grams |
|---|---|
| Dioctylsodiumsulfosuccinate | 1.00 |
| Activated carbon | 10.00 |
| Oxystarch | 25.00 |
| Sucrose | 25.00 |
| Starch | 22.00 |
| Acacia | 7.8 |
| Talc | 3.1 |
| Magnesium stearate | 1.5 |
| Stearic acid | 1.6 |

Mix thoroughly and compress into 100 tablets.

EXAMPLE 13

Eight Wistar rats weighing about 250 g. each on a controlled diet are given daily doses of 2 g. oxystarch, 2 g. activated carbon and 1 mg. diocylsodiumsulfosuccinate by gavage for a period of two weeks. After a 1 week control period with no medication, the same rats are dosed daily with 2 g. oxystarch. Daily fecal nitrogen and weekly blood urea nitrogen and creatinine analyses are made during the total period of the study. During dosing of the combination of oxystarch, activated carbon and diocylsodiumsulfosuccinate, the average daily fecal nitrogen excretion is increased 45% over the control period and 5% over the treatment period with no surfactant.

EXAMPLE 14

One Wistar rat is maintained on a fixed diet for a 1 week controlled period and then is fed daily 1 g. of Norit A activated carbon and 1 mg. of dioctylsodiumsulfosuccinate for 8 days. The average daily fecal nitrogen excretion increases over the control period by 8% during treatment.

EXAMPLE 15

Two uremic dogs on a controlled diet of 5 g./kg. protein plus 70 calories/kg. are given daily doses of 1 g./kg. oxystarch plus 1 g./kg. activated carbon plus 50 mg. diocylsodiumsulfosuccinate (Colase) for a period of 4 weeks. After a control period with no medication, the dogs are fed a daily dose of 1 g./kg. oxystarch for 4 weeks. Daily fecal nitrogen determinations are made during the period of the study. During dosing of the combination of oxystarch, activated carbon and diocylsodiumsulfosuccinate, the average daily fecal nitrogen excretion is increased 104% over the control period and 30% over the treatment period with no surfactant in the two dogs.

EXAMPLE 16

A similar feeding study to that described in Example 13 is performed on 5 rats except that 2 g. activated carbon plus 1 mg. of diocylsodiumsulfosuccinate is given for one dosing period and 2 g. activated carbon alone for the second period with the usual control periods. Analysis of blood and urine creatinine levels shows that the carbon plus surfactant treatment produces the greatest decrease in creatinine levels.

EXAMPLE 17

A similar feeding study to that described in Example 14 is performed except that Amberlite resin (CG-50) is substituted for the oxystarch. The treatment period with the combination of sorbers and surfactant produces the greatest increase in fecal nitrogen excretion.

EXAMPLE 18

When an experiment is carried out similar to Example 15 except that oxycellulose is substituted for oxystarch, the treatment period with the combination of sorbers and surfactant produces the greatest increase in fecal nitrogen excretion.

EXAMPLE 19

Using the same procedure as that of Example 15 and substituting polyacrolein for oxystarch, the greatest amount of fecal nitrogen is excreted when the sorbers and surfactants are present.

EXAMPLE 20

When the procedure of Example 13 is followed, except that N-lauryl-β-aminopropionic acid is substituted for dioctylsodiumsulfosuccinate, the greatest amount of nitrogen is found in the feces when the surfactant and sorbers are both present.

We claim:

1. A method of facilitating the removal of urea, creatinine and ammonia from the intestinal tract of a warm-blooded animal which comprises orally administering to said animal an effective urea, creatinine and ammonia lowering amount of a composition of 1 part dioctyl sodium sulfosuccinate and from 10–10,000 parts of at least one sorbent selected from the group consisting of activated carbon, oxystarch and oxycellulose.

2. A method in accordance with claim 1, wherein the sorbent is activated carbon and oxystarch.

3. A method in accordance with claim 1, wherein the sorbent is oxystarch.

4. A method in accordance with claim 1, wherein the sorbent is activated carbon and oxycellulose.

5. A method in accordance with claim 1, wherein the sorbent is oxystarch and oxycellulose.

* * * * *